(12) United States Patent
Eberle et al.

(10) Patent No.: US 12,102,738 B2
(45) Date of Patent: Oct. 1, 2024

(54) FRAGRANCING DEVICE

(71) Applicant: Mahle International GmbH, Stuttgart (DE)

(72) Inventors: Daniel Eberle, Ludwigsburg (DE); Sham Kasar, Maharashtra (IN); Sven Petzner, Welzheim (DE); Oliver Schultze, Stuttgart (DE)

(73) Assignee: MAHLE INTERNATIONAL GMBH (DE)

( * ) Notice: Subject to any disclaimer, the term of this patent is extended or adjusted under 35 U.S.C. 154(b) by 850 days.

(21) Appl. No.: 17/165,928

(22) Filed: Feb. 2, 2021

(65) Prior Publication Data
US 2021/0236680 A1    Aug. 5, 2021

(30) Foreign Application Priority Data
Feb. 3, 2020    (DE) .......................... 102020201256.3

(51) Int. Cl.
*A61L 9/12*        (2006.01)
*B60H 3/00*        (2006.01)

(52) U.S. Cl.
CPC .............. *A61L 9/12* (2013.01); *B60H 3/0007* (2013.01)

(58) Field of Classification Search
CPC ... A61L 9/00; A61L 9/015; A61L 9/04; A61L 9/12; A61L 2209/00; A61L 2209/10; A61L 2209/13; A61L 2209/133; B60H 3/00; B60H 3/0007
See application file for complete search history.

(56) References Cited

U.S. PATENT DOCUMENTS

| | | | | |
|---|---|---|---|---|
| 4,968,456 A | * | 11/1990 | Muderlak | A61L 9/122 261/DIG. 65 |
| 7,670,566 B2 | * | 3/2010 | Adair | G01N 31/229 392/394 |
| 9,192,691 B2 | * | 11/2015 | Bourne | A61L 9/125 |
| 9,308,287 B2 | | 4/2016 | Wolf et al. | |

(Continued)

FOREIGN PATENT DOCUMENTS

| | | |
|---|---|---|
| CN | 204395064 U | 6/2015 |
| CN | 105579072 A | 5/2016 |
| CN | 107206869 A | 9/2017 |

(Continued)

OTHER PUBLICATIONS

English abstract for EP-2 164 531.
(Continued)

*Primary Examiner* — Natasha E Young
(74) *Attorney, Agent, or Firm* — Fishman Stewart PLLC

(57) ABSTRACT

A fragrancing device is disclosed. The fragrancing device includes a housing having an installation space and a longitudinal housing axis at which a carrier is arranged with contact. The carrier is provided separately with respect to the housing and includes a cover part that covers an installation space opening of the installation space. A carrier part having at least one fragrance cartridge receptacle for receiving a fragrance cartridge is provided. A guide stop is disposed axially in a direction of the housing axis between the carrier and the housing for guiding the carrier as part of a plug-in movement relative to the housing along the housing axis. The guide stop includes a guide pin and a guide pin receptacle.

20 Claims, 4 Drawing Sheets

(56) References Cited

U.S. PATENT DOCUMENTS 10,442,275 B2    10/2019  Quintanar et al.
2016/0236542 A1   8/2016  Stiehler et al.

FOREIGN PATENT DOCUMENTS

| CN | 207081173 U      | 3/2018  |
|----|------------------|---------|
| CN | 108434502 A      | 8/2018  |
| DE | 103 27 122 A1    | 3/2005  |
| DE | 10 2006 022 661 A1 | 11/2007 |
| DE | 10 2007 045 160 A1 | 4/2009  |
| EP | 2 164 531 B1     | 2/2013  |
| JP | H02200268 A      | 8/1990  |

OTHER PUBLICATIONS

English abstract for DE-10 2007 045 160.
English abstract for DE-10 2006 022 661.
English abstract for DE-103 27 122.
Chinese Search Report dated Jul. 22, 2022 and First Office Action dated Jul. 28, 2022 for Chinese Patent Application No. 201101249524.

* cited by examiner

FRAGRANCING DEVICE

CROSS-REFERENCE TO RELATED APPLICATION

This application claims priority to German Application No. DE 10 2020 201 256.3 filed on Feb. 3, 2020, the contents of which are hereby incorporated by reference in its entirety.

TECHNICAL FIELD

The invention relates to a fragrancing device for fragrancing purposes. The fragrancing device has an housing having an installation space and a longitudinal housing axis, at which a carrier is arranged with contact, which carrier is formed separately with respect to the housing and comprises a cover part suitable for covering an installation space opening of the installation space, and comprises a carrier part having at least one fragrance cartridge receptacle for receiving a fragrance cartridge. Axially in the direction of the longitudinal housing axis between carrier and housing, the fragrancing device has a guide stop means for guiding the carrier as part of a plug-in movement relative to the housing along the longitudinal housing axis.

BACKGROUND

Fragrancing devices for the fragrancing of the above-mentioned type are described in an exemplary manner in the documents DE 103 27 122 A1, DE 10 2006 022 661 A1, DE 10 2007 045 160 A1, and EP 2 164 531 B1.

In the case of the known fragrancing devices, which are used in particular to increase the passenger comfort and the vehicle individualization, the fragrance cartridges arranged at the fragrance cartridge receptacles need to be replaced from time to time in order to store a fragrance-emanating fragrance medium, in particular when the fragrance medium is depleted. Due to the usually relatively narrow available installation space inside a road motor vehicle, the installation space package regions, which are available or specified for fragrancing devices, are relatively limited. In addition, there is a desire for keeping the installation space package regions to be relatively flexible, so that fragrancing devices can be arranged at virtually any location in the road motor vehicle. Fragrancing devices are placed, for example, at a wide variety of locations, for example in the dashboard or also in the glove compartment. However, the specified relatively narrow available installation space and the desired flexibility are associated with the problem that the fragrance cartridges, which are arranged at the fragrance cartridge receptacles in the fragrancing devices, are usually relatively difficult to access. The makes the replacement of the fragrance cartridges, which is to be carried out from time to time, more difficult. It is thus desirable to realize the accessibility of the fragrance cartridges and the replacement thereof in a less complex manner.

It is thus the object of the invention to provide an improved or at least another embodiment of a fragrancing device.

In the case of the present invention, this object is solved in particular by the subject matter of the independent claim(s). Advantageous embodiments are subject matter of the dependent claims and of the description.

SUMMARY

It is the basic idea of the invention to install the fragrance cartridge receptacles, which receive the fragrance cartridges, at a carrier, which is formed separately from the housing of the fragrancing device, and to guide said carrier relative to the housing by means of a guide stop means, in order to facilitate a replacement of the fragrance cartridges for an operator. For this purpose, the guide stop means is equipped with at least one guide pin and at least one guide pin receptacle.

In detail, the fragrancing device, which is advantageously arranged at a road motor vehicle and which is used in particular for fragrancing a road motor vehicle interior of the road motor vehicle, has a housing, which has or defines an internal installation space and a longitudinal housing axis, which is arranged in particular in the direction of the main expansion of the housing. The housing advantageously is a cylinder housing, a circular cylinder housing, a conical cylinder housing, or a truncated cone-shaped cylinder housing, or a cylindrical annular housing. As an example, the annular housing has a ring-shaped ring cylinder cross sectional surface area, which is constant throughout, in particular along the longitudinal housing axis with respect to the area and the diameter. The annular housing advantageously furthermore has an annular cylinder wall, which is limited between an outer jacket surface of the housing, which is aligned outwards with respect to the longitudinal housing axis, and an inner jacket surface of the housing, which is aligned inwards with respect to the longitudinal housing axis. The housing, in particular the annular housing, can be made of a plastic, a metallic material, or a composite material. The housing, in particular the annular housing, can serve to protect components of the fragrancing device, in particular to protect against interfering influences, which act from outside the housing, or against dirt, respectively, and/or interfering fluid, and/or electromagnetic radiation. The housing can advantageously form or limit a single-space or multi-space installation space, wherein components of the fragrancing device can be received, in particular loosely inserted temporarily, or firmly arranged virtually permanently, in a house-like manner in the interior of the installation space. At the housing, components of the fragrancing device can furthermore be positioned and/or fixed to the housing with contact from inside the housing and/or from outside the housing, in particular by means of a substance-to-substance bond, in a non-positive manner, and/or in a positive manner. The housing has, for example, positioning means and/or fixing means, which are suitable for this purpose, for example a bearing point and/or fixation points. In particular fragrance components or electric components or further functional components can be components of the fragrancing device. The longitudinal housing axis can be an axis of rotational symmetry.

The fragrancing device furthermore has a carrier, which is formed separately with respect to the housing and which can in particular be moved independently thereof, for example by hand. The carrier, in turn, has a cover part, which is suitable for covering an installation space opening of the installation space, which is oriented towards the surrounding area, and a carrier part, which has a fragrance cartridge receptacle for receiving at least one fragrance cartridge. Cover part and carrier part can be embodied by means of a substance-to-substance bond and integrally. Carrier or cover part and carrier part can be made of a plastic, a metallic material, or a composite material, in particular of the same material as the housing. It is generally conceivable that the cover part is a round cover, which is formed from a dome-shaped and circular middle cover part and an edge bead, which is circumferentially arranged thereon and which protrudes away from the middle cover part in a protrusion-like manner. The edge bead can cooperate in a fluid-tight manner, for example, directly, with a circumferential edge of the installation space opening. For example, an operating handle, which can be accessed from outside the fragrancing device, for example by hand, and by means of which the entire carrier can be operated, in particular in the below-described plug-in movement, can be arranged at the middle cover part. In addition to the fragrance cartridge receptacle, the mentioned carrier part of the carrier can carry further functional components, for example functional components for activating the respective fragrance cartridges. In any case, the fragrance cartridge receptacle can have, for example, several placement spots for receiving a respective single fragrance cartridge. Instead of one fragrance cartridge, a so-called blank can also be received. While the fragrance cartridges each carry a fragrance-emanating fragrance medium, a blank does not carry a fragrance-emanating or a fragrance medium.

The carrier, which can in particular be moved independently of the housing, is now designed such that it can be attached to or inserted into an installation space opening of the installation space of the housing or the housing with contact, with the fragrance cartridge receptacle first, and can be removed from the housing again. On the one hand, this has the effect that the installation space opening of the installation space, which is oriented towards the surrounding area, can be covered in a virtually fluid-tight manner by means of the carrier, in particular by means of the cover part, and that the fragrance cartridges, which are arranged at the fragrance cartridge receptacle, can be inserted into the installation space, so that the fragrancing device can be put into operation. As part of a partial insertion movement of a superordinate plug-in movement, which will be described below, the carrier can thereby be attached or inserted relative to the housing and onto the latter with contact, in particular along the longitudinal housing axis. On the other hand, this has the effect that the carrier can be removed from the housing again, for example in order to replace fragrance cartridges. The fragrancing device advantageously has at least a single, preferably a plurality of fragrance cartridges for receiving a fragrance-emanating fragrance medium.

Axially in the direction of the longitudinal housing axis between carrier and housing or in the region between carrier and housing, the fragrancing device furthermore has a guide stop means for guiding the carrier as part of the plug-in movement relative to the housing, in particular along the longitudinal housing axis or along a specified or specifiable plug-in axis. It is essential for the invention that the guide stop means has at least one guide pin and at least one guide pin receptacle, which is in particular designed to be complementary to the guide pin, by means of which the guidance of the carrier relative to the housing is realized.

This has the effect that the carrier together with the fragrance cartridges can be removed as a whole from the housing, guided by means of the guide stop means, or can be removed from the fragrancing device, respectively. This has the advantage that the fragrance cartridges and the fragrancing device can quasi be separated from one another. The fragrance cartridge replacement is thus no longer dependent on the installation location, whereby an intuitive and simple/uncomplicated fragrance cartridge replacement is realized.

The guide pin and the guide pin receptacle can advantageously engage with one another with contact. They can in particular engage with one another in a slidably or rollably displaceable manner. For this purpose, the guide pin and the guide pin receptacle can either each have sliding surfaces or a rolling surface on the one hand and a rolling assembly, in particular a ball bearing assembly, on the other hand. This has the effect that, as part of a plug-in movement, the carrier can be guided relative to the housing, in particular along the longitudinal housing axis, between an installed state of the carrier, attached completely with contact to the housing, and at least one mounting state of the carrier, spaced apart therefrom in the longitudinal housing axis. This has the advantage that the carrier can optionally be removed from the housing or can be mounted thereto, in particular by an operator, for example in order to arrange one or several fragrance cartridges to the fragrance cartridge receptacle of the carrier.

As part of the plug-in movement, the guide pin and the guide pin receptacle can furthermore abut against one another with contact. This has the effect that a partial insertion movement, which is directed towards the housing, of the carrier can be blocked and that the carrier can be operated into a specified installed state or a specified target position, respectively, relative to the housing. It is thus advantageously ensured that the carrier can be repeatably positioned at a predetermined installed state.

The guide pin can advantageously be formed by a cylinder sleeve having a longitudinal guide pin axis or by a cylinder round rod. The cylinder sleeve is advantageously a circular ring cylinder sleeve, which has a circular ring-shaped cross section, which is constant throughout with respect to the longitudinal guide pin axis. The cylinder round rod has a circular cross section, which is constant throughout with respect to the longitudinal guide pin axis. It goes without saying that the cross sections can be designed to be variable with respect to the longitudinal guide pin axis, the guide pin can in particular have a cross section, which continuously decreases towards a free end, with respect to the longitudinal guide pin axis.

The cylinder sleeve can further advantageously be formed to be slotted. This has the effect that it has slots in a circumferential direction, which is referred to as cylinder sleeve circumferential direction, around the longitudinal guide pin axis. The slots can be arranged so as to be spaced apart differently from one another or equidistantly in the direction of the cylinder sleeve circumferential direction. In any case, the cylinder sleeve can be radially permeated completely by at least one of the slots with respect to the longitudinal guide pin axis. This has the advantage that the cylinder sleeve is slightly optimized with respect to its dead weight. A further advantage is that the slots cooperate with protrusions of the guide pin receptacle, which will be described below, in order to accomplish a centering of the guide pins relative to the guide pin receptacle.

It is advantageous when the cylinder sleeve has at least one cylinder sleeve front face, in particular a circular ring cylinder sleeve front face, which is in particular aligned orthogonally to the longitudinal guide pin axis. The slots can thereby each lead to the cylinder sleeve front face by forming an internal insertion slot opening in the direction of the longitudinal guide pin axis, so that said cylinder sleeve front face is quasi segmented. In any case, at least one slot can be flanked on both sides in the cylinder sleeve circumferential direction by insertion means, which are arranged at the cylinder sleeve and which serve as insertion aid for below-described protrusions. The insertion means in each case extend at least section by section in the direction of the longitudinal guide pin axis directly next to the respective slot. The insertion means can in each case be formed by a lead-in bevel or a lead-in ramp or a lead-in curve.

The cylinder sleeve can have an inner jacket surface and an outer jacket surface aligned opposite thereto. Protrusions, which protrude radially outwards from the cylinder sleeve with respect to the longitudinal guide pin axis can be arranged at the outer jacket surface. The protrusions can be arranged so as to be spaced apart differently from one another or equidistantly in a cylinder sleeve circumferential direction around the longitudinal guide pin axis.

The protrusions can advantageously each have one or several protrusion bevels, protrusion ramps, or protrusion curves. They can each be designed so as to slope radially outwards with respect to the longitudinal guide pin axis.

The guide pin receptacle can furthermore be formed by a cylinder receiving sleeve, in particular a circular ring cylinder receiving sleeve, which has a longitudinal guide pin receptacle axis. The cylinder receiving sleeve can likewise be designed to be slotted. Advantageously, the cylinder receiving sleeve is a circular ring cylinder receiving sleeve, which has a circular ring-shaped cross section, which is constant throughout with respect to the longitudinal guide pin receptacle axis. It goes without saying that the cross section can be designed to be variable with respect to the longitudinal guide pin receptacle axis, towards a free end, the guide pin receptacle can in particular have a cross section, which decreases continuously with respect to the longitudinal guide pin receptacle axis.

The cylinder receiving sleeve can further have an outer jacket receiving surface and an inner jacket receiving surface, which is aligned opposite thereto, wherein positioning protrusions, which protrude radially inwards radially from the cylinder receiving sleeve with respect to the longitudinal guide pin receptacle axis, are arranged at the inner jacket receiving surface. Advantageously, exactly one single positioning protrusion is provided. The positioning protrusions can be arranged so as to be spaced apart differently from one another or equidistantly in a cylinder receiving sleeve circumferential direction around the longitudinal guide pin receptacle axis.

The cylinder receiving sleeve can advantageously have at least one cylinder receiving sleeve front face, which is aligned in particular orthogonally to the longitudinal guide pin axis, in particular a circular ring cylinder receiving sleeve front face. At least one of the above-described positioning protrusions can thereby be arranged with contact at the inner jacket receiving surface such that a distance, in particular a longitudinal distance, is defined between said positioning protrusion and the cylinder receiving sleeve front face in the direction of the longitudinal guide pin receptacle axis. In the alternative, it is also conceivable that one or all of the positioning protrusions are arranged at the inner jacket receiving surface such that they are flush with the cylinder receiving sleeve front face in the direction of the longitudinal guide pin receptacle axis.

The cylinder receiving sleeve can further advantageously have an internal insertion space, which is enclosed at least section by section or completely in a rotating manner, in particular circumferentially, by the inner jacket receiving surface. As part of the partial insertion movement, the cylinder sleeve can be inserted into the insertion space, whereby it dips into the latter, in particular completely. As part of the partial insertion movement, at least one positioning protrusion of the cylinder receiving sleeve can furthermore glide with contact along the insertion means of the cylinder sleeve, so that at least one positioning protrusion of the cylinder receiving sleeve engages with contact with a slot of the cylinder sleeve as part of the partial insertion movement. This has the advantageous effect that the cylinder receiving sleeve can be positioned and/or centered in one of the circumferential directions according to a specified or specifiable angular positioned with respect to the cylinder sleeve.

As part of the partial insertion movement, the cylinder receiving sleeve front face of the cylinder receiving sleeve can slide with contact along at least one protrusion of the cylinder sleeve. This has the desired effect that the cylinder receiving sleeve can be positioned and/or centered with respect to the cylinder sleeve.

To realize an optimal function of the fragrancing device, it can be provided that in the installed state of the carrier, when attached to the housing, the guide pin and the guide pin receptacle are each centrally aligned with respect to the longitudinal housing axis. In this case, the carrier and the housing are centrally aligned with one another or are flush with one another, respectively, so that the carrier can be mounted to the housing. At least in the attached state of the carrier, the longitudinal guide pin axis of the guide pin and the longitudinal guide pin receptacle axis of the guide pin receptacle can furthermore be centrally aligned with respect to the longitudinal housing axis. In this case, the carrier and the housing are also aligned centrally with one another or are flush with one another, respectively, so that the carrier can be mounted to the housing.

The guide pin is advantageously arranged at the housing or at the carrier. In particular an arrangement by means of a substance-to-substance bond or, when the guide pin is provided as separate component, a positive and/or non-positive arrangement is thereby possible.

It is furthermore possible that the guide pin receptacle is arranged at the housing or at the carrier. It is also conceivable here that the guide pin receptacle is provided by means of a substance-to-substance bond at the housing or at the carrier or, when the guide pin receptacle is provided as separate component, is arranged in a positive and/or non-positive manner at the housing or at the carrier.

The guide stop means can advantageously have a locking assembly, which serves to releasably fix the carrier to the housing in the installed state of the carrier. For this purpose, the locking assembly can have male locking parts, which are arranged at the cover part or at an edge cover part of the cover part, which protrudes away from the cover part in a protrusion-like manner. For functional reasons, the locking assembly advantageously has female locking parts, which are arranged at the housing. The male locking parts and the female locking parts can elastically engage with one another at least in the installed state of the carrier. This has the effect that a partial insertion counter movement of the carrier relative to the housing is blocked in a direction opposite to the partial insertion movement along the longitudinal housing axis. This has the advantage that the carrier can be secured to the housing against unintentionally falling out.

The invention also recognized that a push-push system or a clipping can be realized between carrier and housing, which is to make it possible for an operator of the fragrancing device to allow the carrier to move out of the housing without great effort.

In the installed state of the carrier, when attached completely to the housing, in particular during operation of the fragrancing device, the cover part of the carrier can completely cover an internal installation space opening of the installation space. Virtually no fluid can thus flow through between housing and carrier, a leakage is quasi prevented. The fragrancing device can thus be installed at any locations of a road motor vehicle, without resulting in a leakage-related unpleasant smell for road motor vehicle passengers. In order to cover the installation space opening of the installation space completely and in a fluid-tight manner, sealing means can be arranged at the cover part or at a middle cover part of the cover part and/or at the housing. For example, O rings or sealing tapes are conceivable here.

The housing, the guide stop means, and the carrier can be made of a plastic material, of a metallic material, or of a compositive material.

In the context of these documents, the terms "several" are be understood as "exactly two", "at least two", or also as "more than two".

In summary, it should be noted: The present invention preferably relates to a fragrancing device comprising a housing having an installation space and a longitudinal housing axis, at which a carrier is arranged, which comprises a cover part suitable for covering an installation space opening of the installation space, and which comprises a carrier part having at least one fragrance cartridge receptacle for receiving a fragrance cartridge, wherein, between carrier and housing, the fragrancing device has a guide stop means for guiding the carrier as part of a plug-in movement relative to housing along the longitudinal housing axis. It is essential that the guide stop means has a guide pin and a guide pin receptacle.

Further important features and advantages of the invention follow from the subclaims, from the drawings, and from the corresponding figure description on the basis of the drawings.

It goes without saying that the above-mentioned features and the features, which will be described below, cannot only be used in the respective combination, but also in other combinations or alone, without leaving the scope of the present invention.

Preferred exemplary embodiments of the invention are illustrated in the drawings and will be described in more detail in the following description, whereby identical reference numerals refer to identical or similar or functionally identical components.

BRIEF DESCRIPTION OF THE DRAWINGS

In each case schematically.

DETAILED DESCRIPTION

Figure 1:
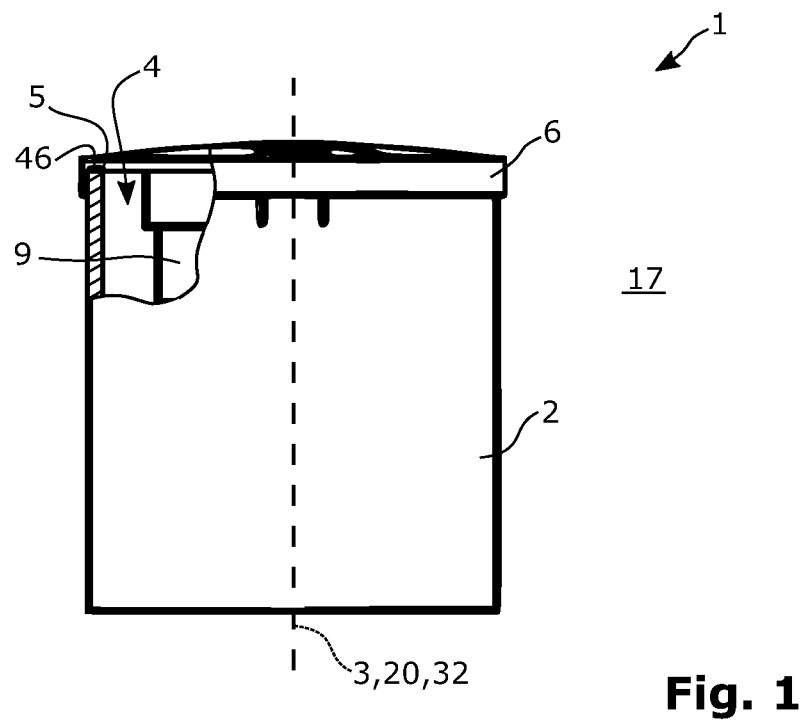
FIG. 1 shows a side view of a preferred exemplary embodiment of a fragrancing device, wherein a carrier of the fragrancing device is arranged at a housing of the fragrancing device, whereby a state is illustrated, which is referred to as installed state.

The drawings 1 to 7 show a fragrancing device 1 for fragrancing, for example a road motor vehicle interior of a road motor vehicle, which is not illustrated in the drawings. For simplicity, functionally identical or functionally similar components are provided with identical reference numerals in the drawings, so that a repeated description of functionally identical or functionally similar components can be forgone, in order to avoid repetitions.

A side view of a preferred exemplary embodiment of a fragrancing device 1 is illustrated in FIG. 1, wherein a carrier 6 of the fragrancing device 1 is arranged with contact at a housing 2 of the fragrancing device 1. A state, which is referred to as installed state 17, is thus illustrated, in which the fragrancing device 1 can be operated, for example.

Advantageously, the housing 2 according to FIG. 1 is a cylinder housing comprising a round or ring-shaped base cross section, so that this can also be referred to as a circular cylinder housing or an annular housing. In detail, it can also be seen in FIG. 1 that the housing 2 has an internal installation space 4, which leads to the surrounding area by forming an internal installation space opening 5. In FIG. 1, the installation space 4 and the installation space opening 5 is illustrated by means of a breakout. The housing 2 further has a longitudinal housing axis 3, which advantageously extends along the main expansion direction of the housing 2. The longitudinal housing axis 3 can form, for example, an axis of symmetry. Insofar as the installation space opening 5 is not covered by the carrier 6, the installation space 4 can be engaged with through the internal installation space opening 5. As will be described below, fragrance cartridges 9 fastened to the carrier 6 can further be inserted into the installation space 4 through the internal installation space opening 5, see in particular FIGS. 1 and 2. It is furthermore conceivable that further fragrancing components of the fragrancing device 1 are arranged at the housing 2. These fragrancing components can advantageously be arranged at the housing 2 from the outside, or can be fastened to the housing 2 from the inside in the interior of the installation space 4. The housing 2 can be formed in multiple pieces or in one piece.

The carrier 6, which is formed separately with respect to the housing 2 and which is thus freely movable relative to the housing 2, for example by hand, and which can optionally be attached to the internal installation opening 5 of the installation space 4 so as to form a cover, has the purpose of covering the installation space opening 5 of the installation space 4 in a completely fluid-tight manner, if possible, and to receive or to carry the fragrance cartridge 9 attached to it such that they protrude into the installation space 4 in the installed state 17, thus when the carrier 6 is arranged at the housing 2. The fragrancing device I can then consequently be operated in the installed state 17, which is illustrated in FIG. 1.

Figure 2:
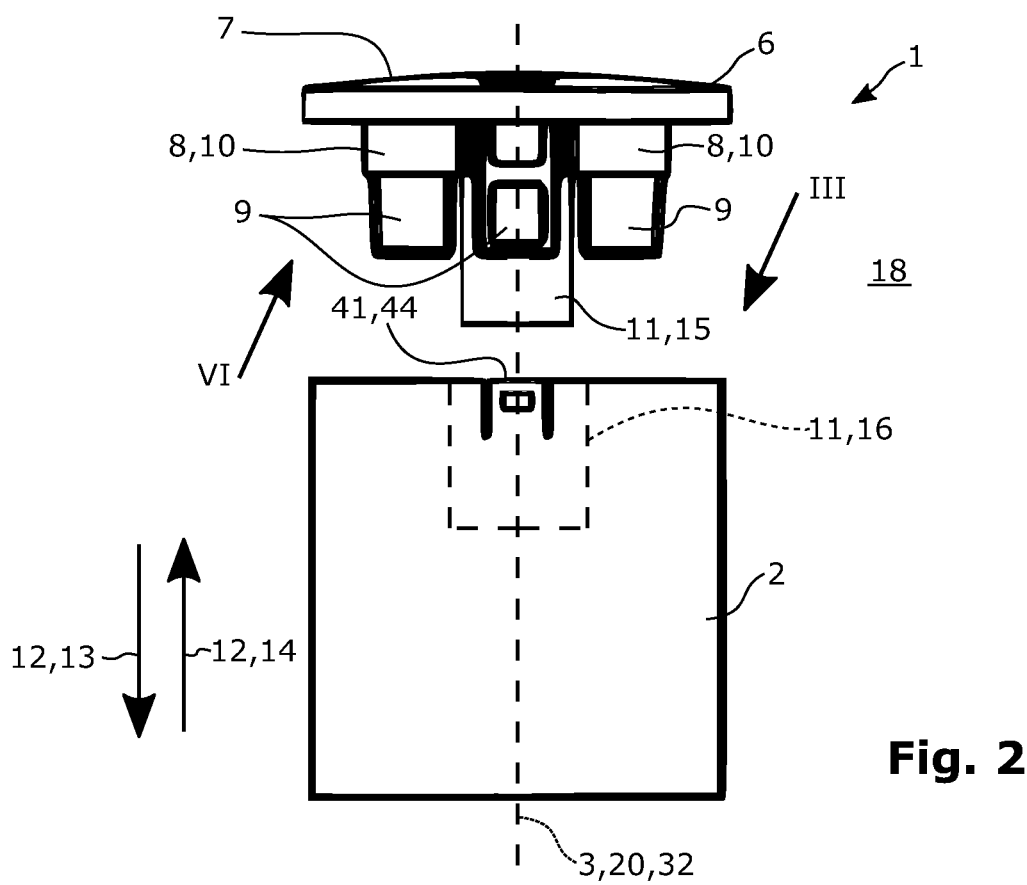
FIG. 2 shows the fragrancing device from FIG. 1 in a side view, wherein the carrier is arranged in the direction of a longitudinal housing axis of the housing at a distance from the housing, whereby a mounting state of the carrier is illustrated, which deviates from the installed state of the carrier.

The fragrancing device 1 from FIG. 1 is shown in FIG. 2 in a side view, wherein the carrier 6 is now arranged spaced apart from the housing 2 in the direction of the longitudinal housing axis 3 of the housing 2. One of several possible mounting states 18 of the carrier 6, which each deviate from the installed state 17 of the carrier 6, is thus illustrated. To realize the function intended for the carrier 6, the carrier 6 has a cover part 7, which is suitable for covering the installation space opening 5, and a carrier part 10, which is suitable for receiving at least one fragrance cartridge receptacle 8 for receiving at least one fragrance cartridge 9. The cover part 7 and the carrier part 10 can be arranged adjacent to one another by means of a substance-to-substance bond, so that the carrier 6 is quasi realized as integral component.

It can also be seen in FIG. 2 that, axially in the direction of the longitudinal housing axis 3 between the carrier 6 and the housing 2, the fragrancing device 1 has a guide stop means 11. Said guide stop means serves to guide the carrier 6 as part of a plug-in movement 12, which is suggested in FIG. 2 by means of a double arrow, as part of which the carrier 6 can be moved relative to the housing 2 along the longitudinal housing axis 3 between the installed state 17 of the carrier 6 and deviating mounting states 18 of the carrier 6. So that the guide function of the guide stop means 11 is ensured, it is provided that the guide stop means 11 has a guide pin 15, which is arranged on the cover side, in particular at the cover part 7, and a guide pin receptacle 16, which is arranged on the housing side, in particular at the housing 2, as suggested by means of a dashed line in FIG. 2. The illustrated guide pin 15 can be engaged with contact in a slidably displaceable manner with the guide pin receptacle 16, in order to move the carrier 6 in a slidably displaceable manner as part of the plug-in movement 12.

Figure 3:
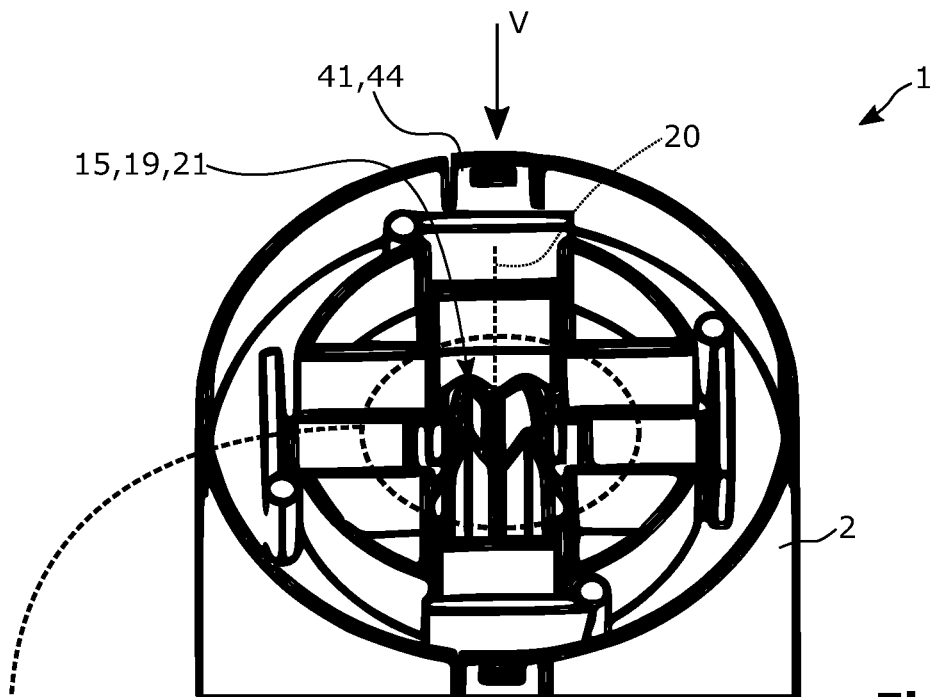
FIG. 3 shows a perspective view obliquely from above onto the fragrancing device from FIG. 2 according to an arrow III entered there, wherein the carrier is removed for better visibility of the housing.
Figure 4:
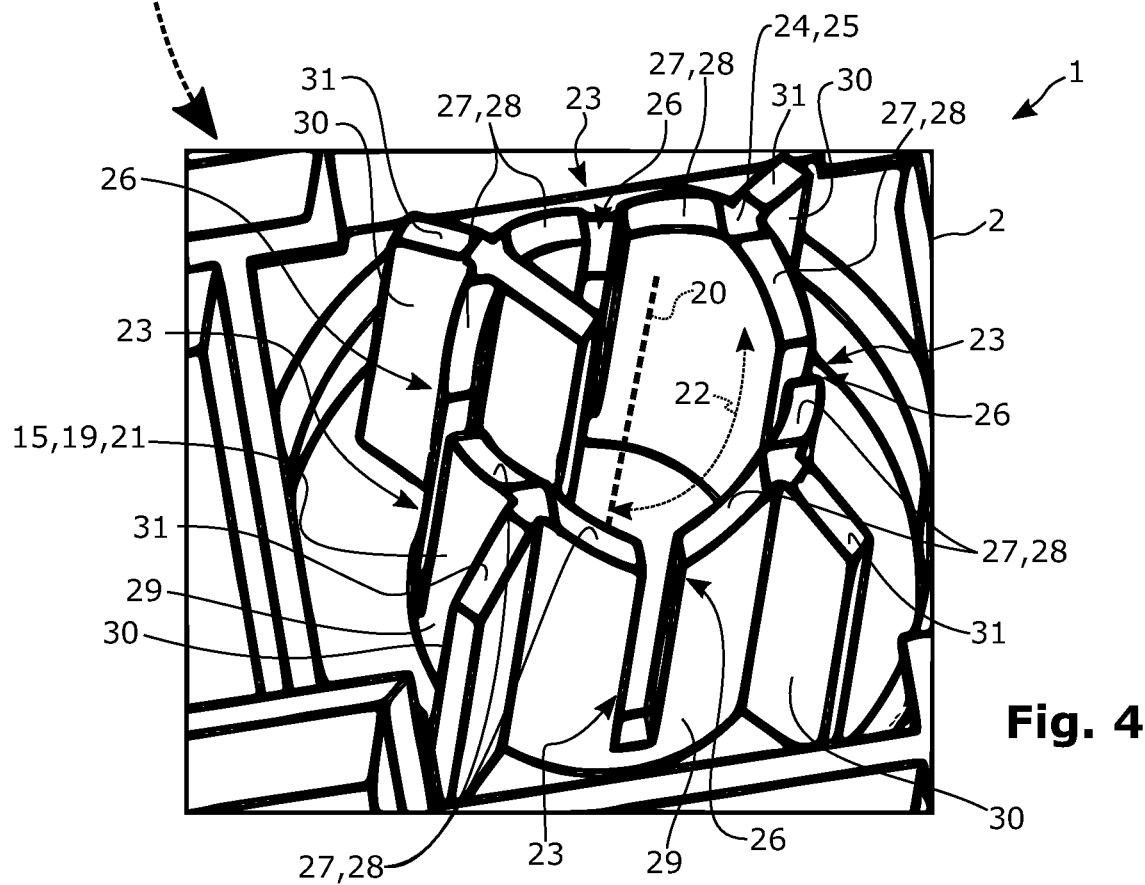
FIG. 4 shows a perspective detail view of the fragrancing device from FIG. 3, according to a section framed by a dotted line in FIG. 3.

In a perspective view, FIG. 3 shows a view obliquely from above onto the fragrancing device from FIG. 2 according to an arrow III entered there, wherein the carrier 6 is completely removed for better visibility of the housing 2, for example it is in one of the mounting states 18. The view onto the housing 2 shows in particular the guide pin 15, which is illustrated in FIG. 4 in an enlarged perspective detail view: The guide pin 15 can be formed by a cylinder sleeve 19, which can be designed, as an example, as circular ring cylinder sleeve 21, and which can have a circular ring-shaped cross section throughout. Along its main expansion direction, the guide pin 15 defines a longitudinal guide pin axis 20.

It can in particular be seen in FIG. 4 that the cylinder sleeve 19 is embodied to be slotted. This is so, because it has internal slots 23, which are arranged equidistantly from one another, in a cylinder sleeve circumferential direction 22 in a circular manner around the longitudinal guide pint axis 20 and in the direction of the cylinder sleeve circumferential direction 22. The cylinder sleeve 19 thereby defines at least one cylinder sleeve front face 24, which faces away from the housing, in particular a circular ring cylinder sleeve front face 25, into which the slots 23 lead, in each case by forming an internal insertion slot opening 26 in the direction of the longitudinal guide pin axis 20. At least one slot 23 is flanked in a frame-like manner in the cylinder sleeve circumferential direction 22 on both sides introducers or by insertion means 27 (hereafter "insertion means"), which are arranged at the cylinder sleeve 19. The insertion means 27 extend, for example, in the direction of the longitudinal guide pin axis 20 along the respective slot 23 to the cylinder sleeve front face 24, where they can transition into the latter. As illustrated in particular in FIG. 4, the insertion means 27 can thereby in each case be formed by a lead-in bevel 28 or a lead-in ramp or a lead-in curve.

Figure 5:
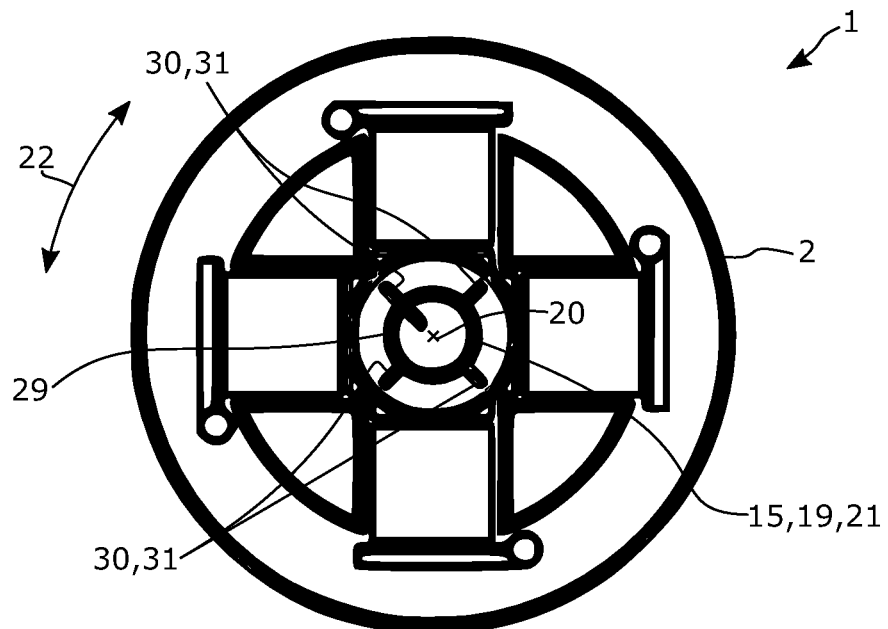
FIG. 5 shows a top view onto the housing from FIG. 3 according to an arrow V entered there, wherein the carrier is again removed for the benefit of better visibility of the housing.

In a top view onto the housing 2 according to an arrow V entered in FIG. 3, FIG. 5 furthermore shows that the cylinder sleeve 19 has a plurality of protrusions 30, which are arranged at an outer jacket surface 29 of the cylinder sleeve 19, which is oriented radially outwards and which, with respect to the longitudinal guide pin axis 20, is only suggested by a small crosshair line in FIG. 5. With respect to the longitudinal guide pin axis 20, the protrusions 30 protrude radially outwards away from the longitudinal guide pin axis 20. The protrusions 30 can furthermore be spaced apart equidistantly from one another in the above-mentioned cylinder sleeve circumferential direction 22 around the longitudinal guide pin axis 20. In an exemplary manner, the protrusions 30 span an angle of approx. 90° between one another in the cylinder sleeve circumferential direction 22. The outer jacket surface 29 and the protrusions 30 are also illustrated in FIG. 4.

It can further be seen in FIGS. 4 and 5 that each protrusion 30 has a protrusion bevel 31 or a protrusion ramp or a protrusion curve. The protrusion bevel 31 is designed so as to slope radially outwards with respect to the longitudinal guide pin axis 20.

Figure 6:
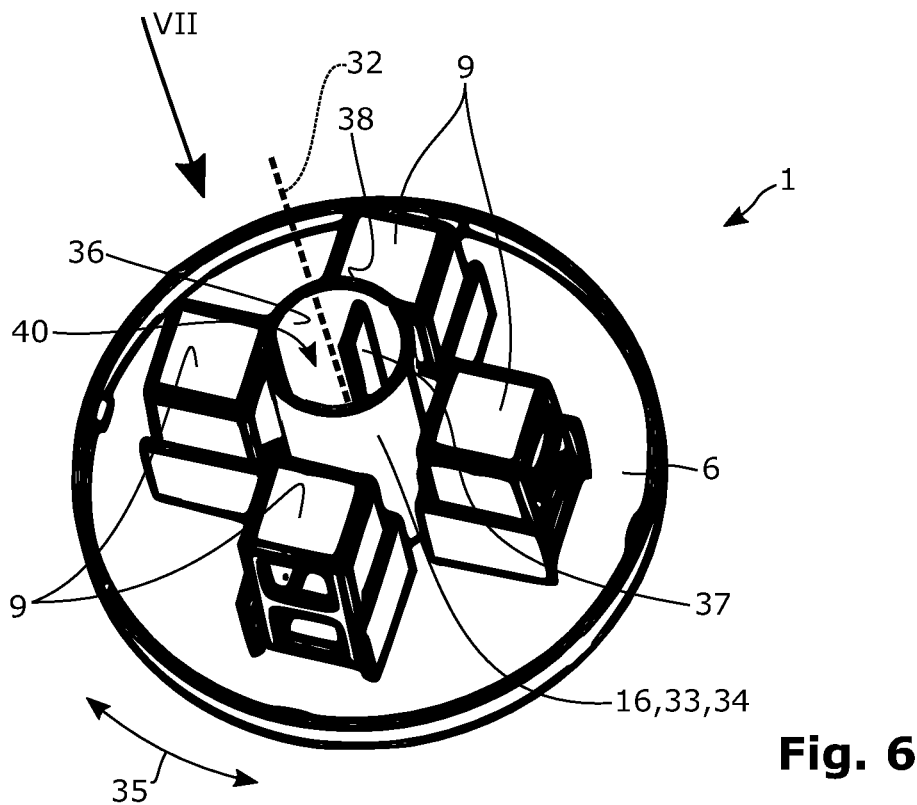
FIG. 6 shows the carrier obliquely from below in a perspective view according to an arrow VI entered in FIG. 2, wherein the housing is now removed for the benefit of better visibility of the carrier, and lastly
Figure 7:
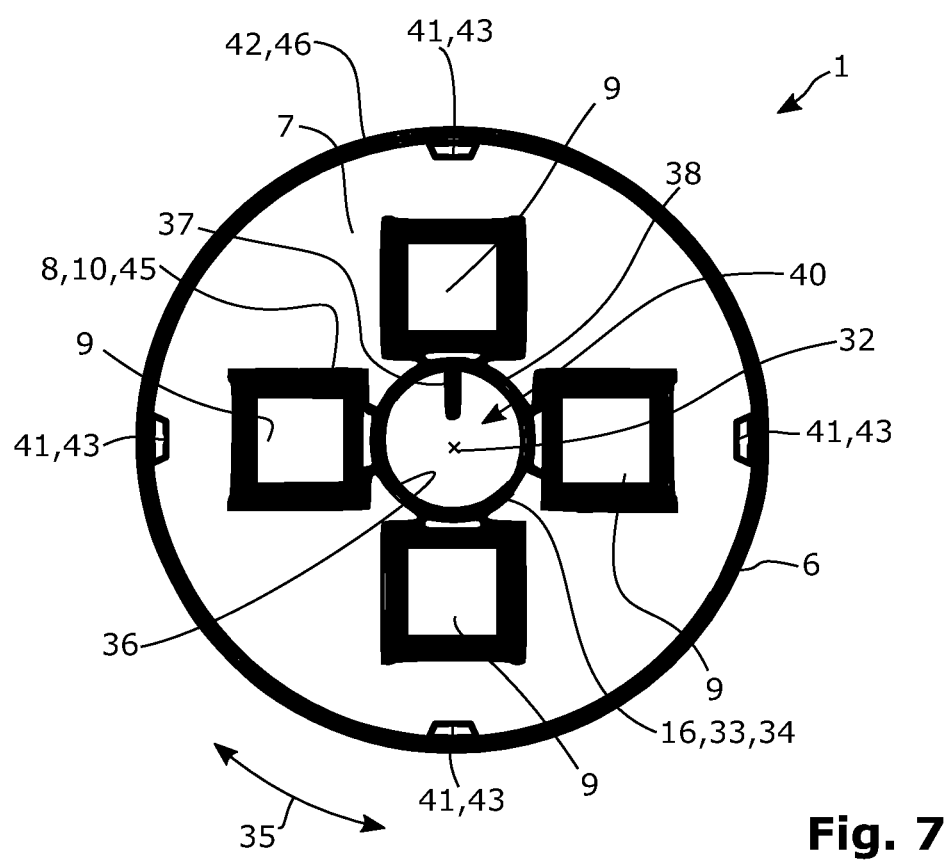
FIG. 7 shows the carrier from FIG. 6 in a top view according to an arrow VII entered there, wherein the housing is again removed for the benefit of better visibility of the carrier.

In a perspective view, FIG. 6 shows the carrier 6 with view obliquely from below according to an arrow VI entered in FIG. 2, so that in particular the fragrance cartridges 9 can be seen. In a top view, FIG. 7 shows the carrier 6 according to an arrow VII entered in FIG. 6. The housing 2 is thereby in each case removed for the benefit of better visibility of the carrier 6. In particular the guide pin receptacle 16 can be seen in FIG. 6 as well as in FIG. 7. The guide pin receptacle 16 is formed by a cylinder receiving sleeve 33, which has a longitudinal guide pin receptacle axis 32, as an example, this can also be a circular ring cylinder receiving sleeve 34 with circular ring-shaped base cross section. The cylinder receiving sleeve 33 has an inner jacket receiving surface 36, which is oriented inwards with respect to the longitudinal guide pin receptacle axis 32. At least one positioning protrusion 37, which protrudes radially inwards with respect to the longitudinal guide pin receptacle axis 32, can be arranged at the inner jacket receiving surface 36. As can be seen in FIG. 5, the positioning protrusion 37 is fastened to the inner jacket receiving surface 36 such that it is arranged with longitudinal distance in the direction of the longitudinal guide pin receptacle axis 32 to a cylinder receiving sleeve front face 38 of the cylinder receiving sleeve 33, in particular a circular ring cylinder receiving sleeve front face 39.

It can be seen in FIG. 6 as well as in FIG. 7 that the cylinder receiving sleeve 33 defines an internal insertion space 40, which is enclosed in a rotating manner by the inner jacket receiving surface 36 in the direction of a cylinder receiving sleeve circumferential direction 35 revolving around the longitudinal guide pin receptacle axis 32, and into which the cylinder sleeve 19 can be inserted so as to dip in as part of a partial insertion movement 13 of the plug-in movement 12 along the longitudinal housing axis 3, see also FIG. 2. As part of the partial insertion movement 13, the positioning protrusion 37 can advantageously slide with contact along the insertion means 27 of the cylinder sleeve 19, so as to likewise engage with contact in a sliding manner with a slot 23 of the cylinder sleeve 19 as part of the partial insertion movement 13, wherein the carrier 6 centers and/or positions itself with respect to the housing 2 in one of the circumferential directions 22, 35 according to a specified or specifiable angular position. As part of the partial insertion movement 13, the cylinder receiving sleeve front face 38 can moreover slide with contact along at least one protrusion 30 of the cylinder sleeve 19, in order to center and/or to position the carrier 6 with respect to the housing 2. This has the effect that the carrier 6 can be moved in a reliable manner into a specified or specifiable angular position with respect to the housing 2. This furthermore has the effect that the carrier 6 can be guided towards the housing 2 parallel to the longitudinal housing axis 3 with respect to the housing 2.

The guide pin 15 and the guide pin receptacle 16 can additionally each be centrally aligned with one another with respect to the longitudinal housing axis 3 at least in the installed state 17 of the carrier 6 at the housing 2, see in particular FIG. 1, so that the longitudinal guide pin axis 20 of the guide pin 15 and the longitudinal guide pin receptacle axis 32 of the guide pin receptacle 16 are in particular coaxial to one another.

It can be seen in FIGS. 2, 3, and 7 that the guide stop means 11 of the fragrancing device 1 has a locking assembly, which is labeled in its entirety with reference numeral 41, for releasably fixing the carrier 6 to the housing 2 in the installed state 17 of the carrier 6. The locking assembly 41 can have male locking parts 43, which are arranged integrally at the cover part 7, there in particular at an edge cover part 42 of the cover part 7, or integrally at an edge bead of the cover part 7. The locking assembly 41 can further have female locking parts 44, which are arranged integrally at the housing 2 and which cooperate elastically with the male locking parts 43 in a clamping or locking manner, at least in the installed state 17 of the carrier 6. The male locking parts 43 and the female locking parts 44 can in particular elastically engage with one another, in order to block a partial insertion counter movement 14 suggested in FIG. 2 of the carrier 6 relative to the housing 2 in a direction opposite to the partial insertion movement 13 along the longitudinal housing axis 3 away from the housing 2. This offers the advantageous effect that the carrier 6 is secured to the housing 2, for example against unintentionally falling out.

Finally, it should be pointed out that a sealing means 46 can be arranged at the cover part 7 or at a middle cover part 45 of the cover part 7 and/or at the housing 2, in order to cover the internal installation space opening 5 of the installation space 4 in a complete and fluid-tight manner, see in particular FIGS. 1 and 7.

The invention claimed is:

1. A fragrancing device, comprising:
a housing having an installation space and a longitudinal housing axis, and a carrier arranged at the housing with contact, the carrier formed separately with respect to the housing and includes a cover part structured and arranged to cover an installation space opening of the installation space, and a carrier part having at least one fragrance cartridge receptacle for receiving a fragrance cartridge,
a guide stop disposed axially in a direction of the longitudinal housing axis between the carrier and the housing for guiding the carrier as part of a plug-in movement relative to the housing along the longitudinal housing axis,
wherein the guide stop includes a guide pin and a guide pin receptacle.

2. The fragrancing device according to claim 1, wherein the guide pin and the guide pin receptacle engage with one another with contact in a slidably displaceable manner to guide the carrier as part of the plug-in movement relative to the housing along the longitudinal housing axis between an installed state of the carrier, arranged or inserted completely at the housing, and mounting states spaced apart therefrom in the longitudinal housing axis.

3. The fragrancing device according to claim 1, wherein the guide pin is a cylinder sleeve having a longitudinal guide pin axis.

4. The fragrancing device according to claim 3, wherein the cylinder sleeve is slotted to provide slots that are arranged equidistantly spaced apart from one another in a cylinder sleeve circumferential direction around the longitudinal guide pin axis and in a direction of the cylinder sleeve circumferential direction.

5. The fragrancing device according to claim 4, wherein the cylinder sleeve has at least one cylinder sleeve front face, wherein the slots each lead to the at least one cylinder sleeve front face by forming an internal insertion slot opening in a direction of the longitudinal guide pin axis, and wherein at least one of the slots is flanked in a frame-like manner on both sides in the cylinder sleeve circumferential direction by introducers that are arranged at the cylinder sleeve and which extend at least section by section in the direction of the longitudinal guide pin axis along the at least one slot.

6. The fragrancing device according to claim 5, wherein the introducers are defined by a lead-in bevel or a lead-in ramp or a lead-in curve.

7. The fragrancing device according to claim 3, wherein the cylinder sleeve has an outer jacket surface and protrusions arranged at the outer jacket surface, the protrusions protrude radially outwards with respect to the longitudinal guide pin axis and are spaced apart equidistantly from one another in a cylinder receiving sleeve circumferential direction around the longitudinal guide pin axis.

8. The fragrancing device according to claim 7, wherein the protrusions each have a protrusion bevel or a protrusion ramp or a protrusion curve that slopes radially outwards with respect to the longitudinal guide pin axis.

9. The fragrancing device according to claim 1, wherein the guide pin receptacle is a cylinder receiving sleeve that has a longitudinal guide pin receptacle axis.

10. The fragrancing device according to claim 9, wherein the cylinder receiving sleeve has an inner jacket receiving surface and at least one positioning protrusion arranged at the inner jacket receiving surface, the at least one positioning protrusion protrudes radially inwards with respect to the longitudinal guide pin receptacle axis.

11. The fragrancing device according to claim 10, wherein the cylinder receiving sleeve has at least one cylinder receiving sleeve front face with respect to which a positioning protrusion is arranged at the inner jacket receiving surface with a longitudinal distance in a direction of the longitudinal guide pin receptacle axis.

12. The fragrancing device according to claim 5, wherein the cylinder receiving sleeve defines an internal insertion space that is enclosed at least section by section in a rotating manner by the inner jacket receiving surface, and into which the cylinder sleeve can be inserted so as to dip in as part of the partial insertion movement of the plug-in movement, wherein, as part of the partial insertion movement, at least one positioning protrusion of the cylinder receiving sleeve slides with contact along the introducer of the cylinder sleeve, and wherein, as part of the partial insertion movement, the at least one positioning protrusion of the cylinder receiving sleeve engages with contact with a slot of the cylinder sleeve to at least one of center and position the cylinder receiving sleeve with respect to the cylinder sleeve in one of a cylinder sleeve circumferential direction and a cylinder receiving sleeve circumferential direction according to a specified or specifiable angular position.

13. The fragrancing device according to claim 11, wherein as part of the partial insertion movement, the cylinder receiving sleeve front face slides with contact along at least one protrusion of the cylinder sleeve to at least one of center and position the cylinder receiving sleeve with respect to the cylinder sleeve.

14. The fragrancing device according to claim 1, wherein:
at least in the installed state of the carrier, when attached to the housing, the guide pin and the guide pin receptacle are each centrally aligned with respect to the longitudinal housing axis, or at least in the installed state of the carrier, the longitudinal guide pin axis of the guide pin and the longitudinal guide pin receptacle axis of the guide pin receptacle are centrally aligned with respect to the longitudinal housing axis.

15. The fragrancing device according to claim 1, wherein one of:

the guide pin is arranged at the housing or at the carrier, the guide pin is arranged via a substance-to-substance bond at the housing or at the carrier, and the guide pin is provided as a separate component and is arranged in at least one of a positive and non-positive manner at the housing or at the carrier.

16. The fragrancing device according to claim 1, wherein one of:

the guide pin receptacle is arranged at the housing or at the carrier, the guide pin receptacle is arranged via a substance-to-substance bond at the housing or at the carrier, and the guide pin receptacle is provided as a separate component and is arranged in at least one of a positive and a non-positive manner at the housing or at the carrier.

17. The fragrancing device according to claim 1, wherein the guide stop includes a locking assembly for releasably fixing the carrier to the housing in the installed state of the carrier.

18. The fragrancing device according to claim 17, wherein the locking assembly has male locking parts that are arranged at the cover part or at an edge cover part of the cover part, the male locking parts elastically engage with one another at least in the installed state of the carrier to block a partial insertion counter movement of the carrier relative to the housing in a direction opposite to the partial insertion movement along the longitudinal housing axis to secure the carrier to the housing against unintentionally falling out.

19. The fragrancing device according to claim 1, wherein at least one of:

in the installed state of the carrier, when attached completely to the housing, the cover part of the carrier completely covers an internal installation space opening of the installation space, and a sealing element is arranged at the cover part or at a middle cover part of the cover part, so that in the installed state, the cover part covers the internal installation space opening of the installation space completely and in a fluid-tight manner.

20. The fragrancing device according to claim 1, wherein the guide pin is a circular ring cylinder sleeve having a circular ring-shaped cross section.

\* \* \* \* \*